(12) United States Patent
Bastia

(10) Patent No.: US 8,721,320 B2
(45) Date of Patent: May 13, 2014

(54) DEVICE FOR STRETCHING AN ELASTIC RING

(75) Inventor: Filippo Bastia, Carpi (IT)

(73) Assignee: THD S.p.A., Correggio (IT)

( * ) Notice: Subject to any disclaimer, the term of this patent is extended or adjusted under 35 U.S.C. 154(b) by 369 days.

(21) Appl. No.: 13/193,382

(22) Filed: Jul. 28, 2011

(65) Prior Publication Data
US 2012/0009295 A1 Jan. 12, 2012

Related U.S. Application Data

(63) Continuation-in-part of application No. 13/145,703, filed as application No. PCT/IB2010/050932 on Mar. 4, 2010, now abandoned.

(30) Foreign Application Priority Data

Mar. 12, 2009 (IT) .............................. RE2009A0023

(51) Int. Cl.
*B28B 11/00* (2006.01)
(52) U.S. Cl.
USPC ........... 425/395; 425/383; 606/136; 606/137; 606/139; 606/140

(58) Field of Classification Search
USPC ........... 425/383, 395; 606/136, 137, 139, 140
See application file for complete search history.

(56) References Cited

U.S. PATENT DOCUMENTS 6,482,213 B1 11/2002 Riza

FOREIGN PATENT DOCUMENTS

| DE | 92 05 453 U1 | 6/1992 |
| WO | 00/03642 A1 | 1/2000 |

*Primary Examiner* — Joseph Del Sole
*Assistant Examiner* — John Robitaille
(74) *Attorney, Agent, or Firm* — Pearne & Gordon LLP

(57) ABSTRACT

A device for stretching a plastic ring which comprises pushing means (2) and a loading body (5) which are reciprocally slidable across a plurality of ribs (4) solidly constrained to the pushing means (2), and a plurality of grooves (6) afforded on the loading body (5). The loading body (5) exhibits a first substantially conical portion (7) exhibiting a base (7a), having an external diameter (D) and an apex (7b). The loading body (5) further comprises a second portion (8), contiguous to the first conical portion (7) and exhibiting a proximal end (8a) and a distal end (8b).

14 Claims, 4 Drawing Sheets

DEVICE FOR STRETCHING AN ELASTIC RING

TECHNICAL FIELD

The invention relates to a device for stretching an elastic ring, and is particularly applicable for treatment of haemorrhoidal complaints.

BACKGROUND ART

The prior art describes pistol-type guns for releasing elastic rings (rubber bands) comprising a command tube connected to a gripping handle for manoeuvring, supporting one or more rubber rings to be released.

The command tube comprises an internal tube on a free end of which the rubber ring is predisposed, and an external tube moved in advancement with respect to the internal tube in order to determine release of the rubber ring. The handle is fixed to the internal tube and exhibits a trigger which can be manually activated by an operator in order to command the advancement of the external tube.

For loading the rubber rings, substantially conical tips are known, which are designed to be coupled on the tip of the releasing piston of the rubber ring.

An example of these devices is described in patent DE9205453, which illustrates a device for stretching a rubber ring.

The device comprises a tip, exhibiting at least a conical tract and a cylindrical tract, provided with a plurality of sliding guides.

The device is completed by pushing means slidable along the tip by means of a plurality of ribs that are translatable internally of the corresponding plurality of guides.

Devices of the above-described type exhibit some drawbacks.

Firstly the geometric conformation of the tip requires special attention by the operator during the loading stage.

The application of the ring requires complete sliding of the pushing means from the start to the end of the tip in order to force the ring to stretch.

As it has to cross progressively-increasing transversal sections of the tip, the rubber ring requires a prolonged application of the pushing means to reach the housing seating.

If there should be a distancing of the pushing means from the rubber ring, due for example to a moment of distraction on the part of the user, the ring slides back from the previously-assumed position.

In the same way, even the initial portion of the tip exhibits drawbacks as far as the ring loading operations are concerned.

The operator performing the pre-loading of the ring on the first cylindrical tract of the tip might find that the ring frees itself of its positioning and falls to earth, which means the operator will have to take a new ring and perform the loading operation once more.

Also, the fact that the terminal portion of the tip is provided with a first and a second cylindrical tracts, the second having a smaller diameter than the first which is destined to insert into the release pistol, constitutes a drawback for the operations of locating the ring in the housing seating afforded on the release device.

The operator who is abuttingly locating the end of the releasing device on the broadening of section of the two cylindrical tracts might, due to a distancing of the tip, cause the rubber ring not to abut correctly on the release pistol, but rather have it fall onto the second cylindrical tract.

In the above-described situation, the operation of recuperating the rubber ring is disadvantageously difficult for the operator to perform, as the ring is solidly anchored to the cylindrical tract of the tip.

In this context, the technical objective underlying the present invention is to provide a device for stretching an elastic-material (rubber) ring which obviates the drawbacks in the above-cited prior art.

In particular, an aim of the present invention is to provide a device for stretching an elastic ring which facilitates loading operations of the rubber ring.

A further aim of the present invention is to provide a device for stretching a rubber ring which facilitates the operator's work during the pre-loading stage.

A further aim of the present invention is to provide a device for stretching a rubber ring which provides the operator with a facilitated loading of the ring on the release pistol.

A further aim of the present invention is to provide a device for stretching a rubber ring which, in a case of wrong loading of the ring, enables the operator to recuperate the ring simply and immediately.

The set technical objective and the specified aims are substantially attained by a device for stretching a rubber ring comprising the technical characteristics set out in one or more of the appended claims.

DISCLOSURE OF INVENTION

Further characteristics and advantages of the present invention will better emerge from the non-limiting description that follows of a preferred but not exclusive embodiment of a device for stretching a rubber ring, as it is illustrated in the accompanying figures of the drawings, in which.

Figure 1:
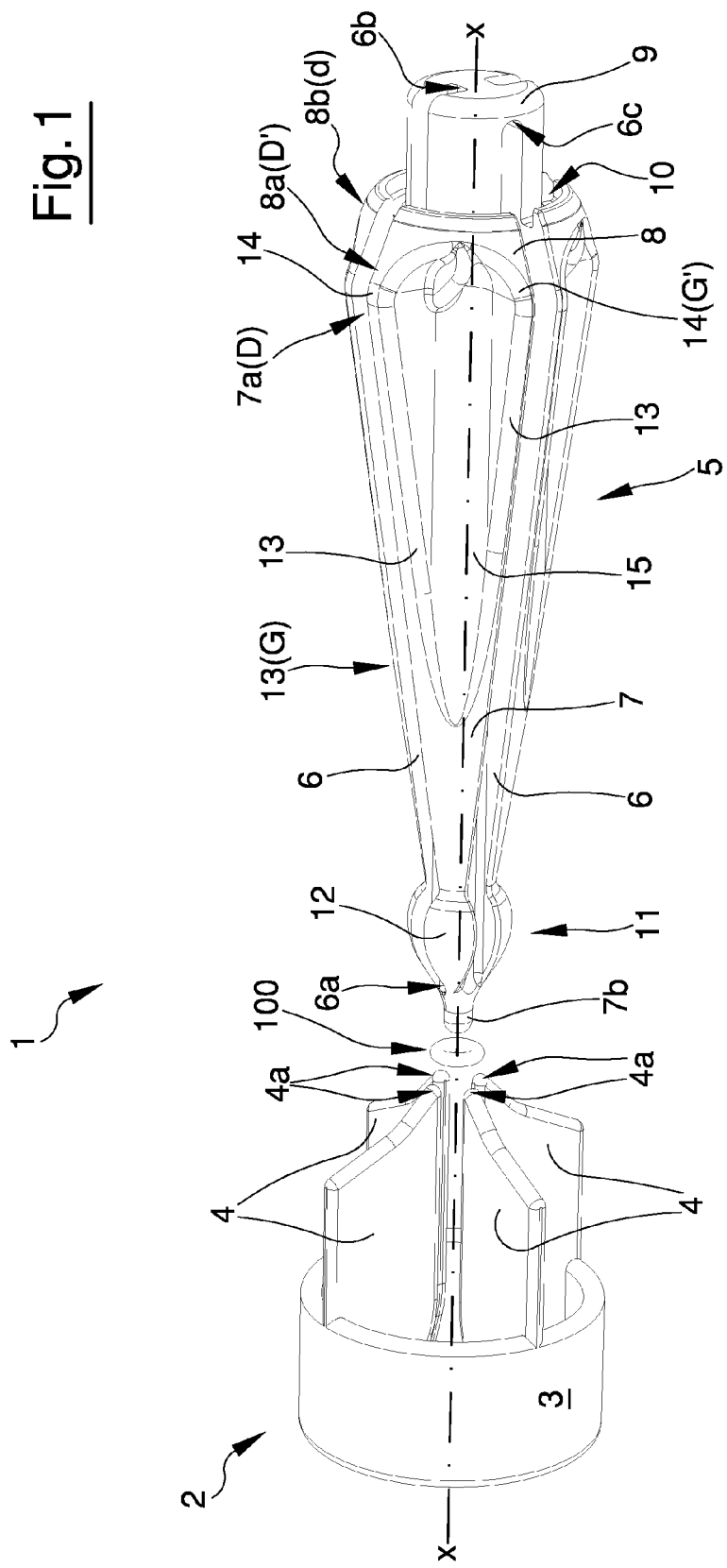
FIG. 1 is a lateral view of a device of the present invention.
Figure 2:
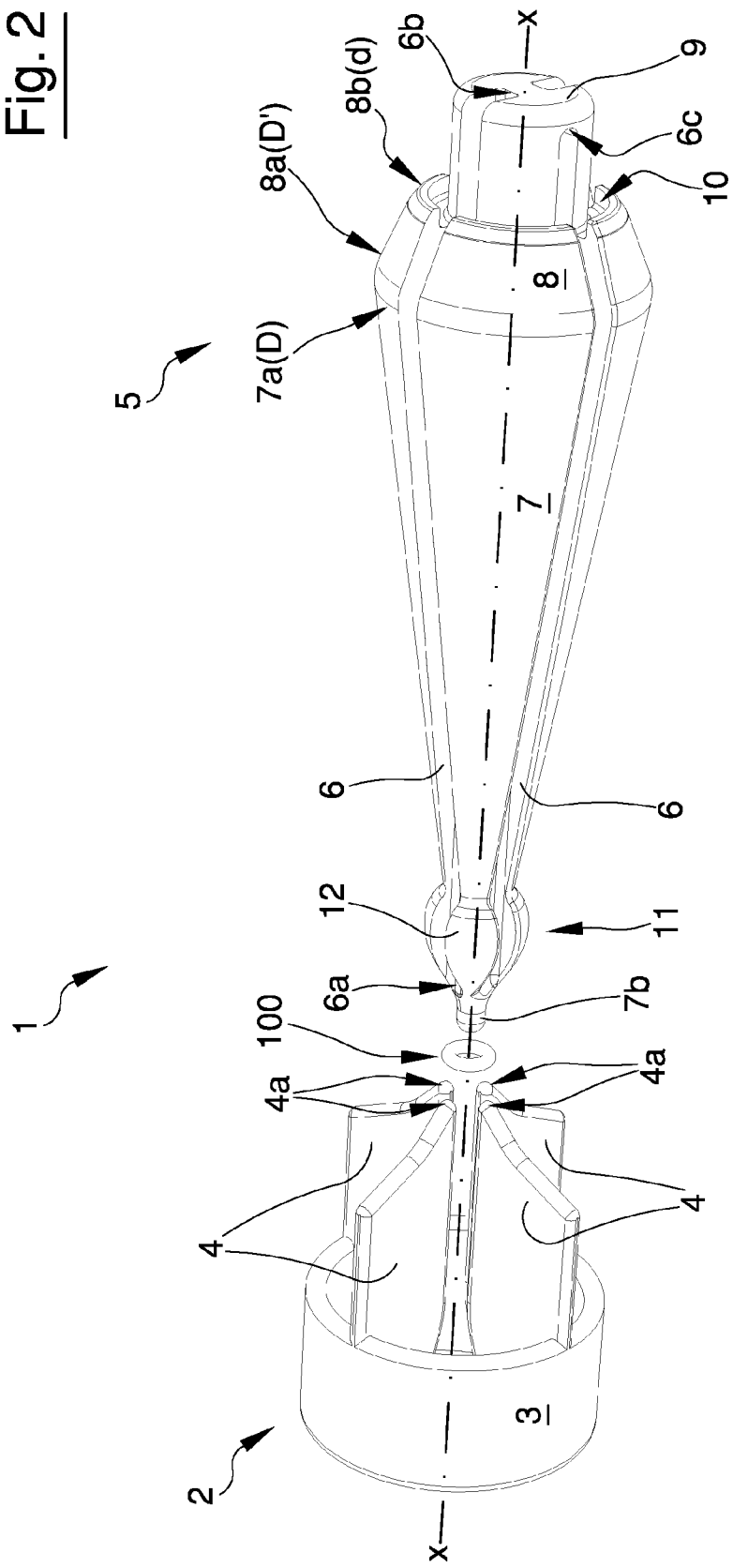
FIG. 2 is a lateral view of a second embodiment of the device of FIG. 1 in accordance with the present invention.

With reference to the figures, 1 denotes in its entirety a device for stretching a rubber ring 100 of the present invention.

The device is applicable in loading rubber rings on a release piston for legating tissues such as, for example, the anal mucosa of a patient.

The invention is advantageously applied in treatment of haemorrhoidal complaints related to the mucosa.

The device 1 comprises a loading body 5 and pushing means 2, the pushing means 2 being slidable on the body 5 in order to load at least a rubber ring 100 thereon.

The pushing means 2 comprise a hollow body 3 internally of which a plurality of ribs 4 develop.

The hollow body 3 preferably exhibits a tubular shape.

The hollow body 3 exhibits an internal diameter which is greater than the external diameter of the loading body 5 in order to facilitate sliding of the loading body 5 internally of the pushing means 2.

As can be seen in the accompanying figures, the plurality of ribs 4 exhibits, starting from the inside of the hollow body 3, a radial development towards the centre of the hollow body 3.

The plurality of ribs 4 is uniformly spaced over the circumference of the hollow body 3, preferably resulting in at least four ribs.

The four ribs are staggered by 90 degrees to one another over the circumference of the hollow body 3.

Each rib 4 has a substantially rectangular edge terminating on a portion which faces the loading body 5 with a respective peak 4a.

Each peak 4a enters into contact with the elastic ring 100 and, during the rising thereof along the loading body 5, collaborates with respective grooves 6 afforded on the loading body and more fully described herein below, to push the ring 100.

The loading body 5 exhibits a development direction along a prevalent direction X-X.

The loading body 5 exhibits a plurality of grooves 6, each having an orientation which is parallel to the prevalent direction X-X in order to facilitate sliding, along direction X-X, of the plurality of ribs 4 of the pushing means 2.

Each groove of the plurality of grooves 6 exhibits a radial progression.

Each groove of the plurality of grooves 6 extends uniformly on the loading is body 5 and is preferably spaced from a preceding and a following groove by 90 degrees.

The loading body 5 comprises a substantially conical first portion 7, a second portion 8, located downstream of the first portion 7, and a cylindrical portion 9, located downstream of the second portion 8.

The substantially conical first portion 7 exhibits a base 7a having an external diameter D and an apex 7b. The second portion exhibits a proximal end 8a and a distal end 8b. The proximal end 8a exhibits an external diameter D' and the distal end 8b exhibits an external diameter d.

The external diameter D' of the proximal end 8a is greater than the external diameter d of the distal end 8b.

As can be seen in the figures, the second portion 8 preferably exhibits a truncoconical shape.

However, without forsaking the ambit of protection of the following invention, the second portion 8 exhibits, starting from the external diameter D of the base 7 of the first substantially conical zone 7, a section having a decreasing progression.

In other words the second portion 8 exhibits, from the proximal end 8a to the distal end 8b, a tapering transversal section.

The proximal end 8a of the second conical portion 8 faces the first substantially conical portion 7.

Figure 4:
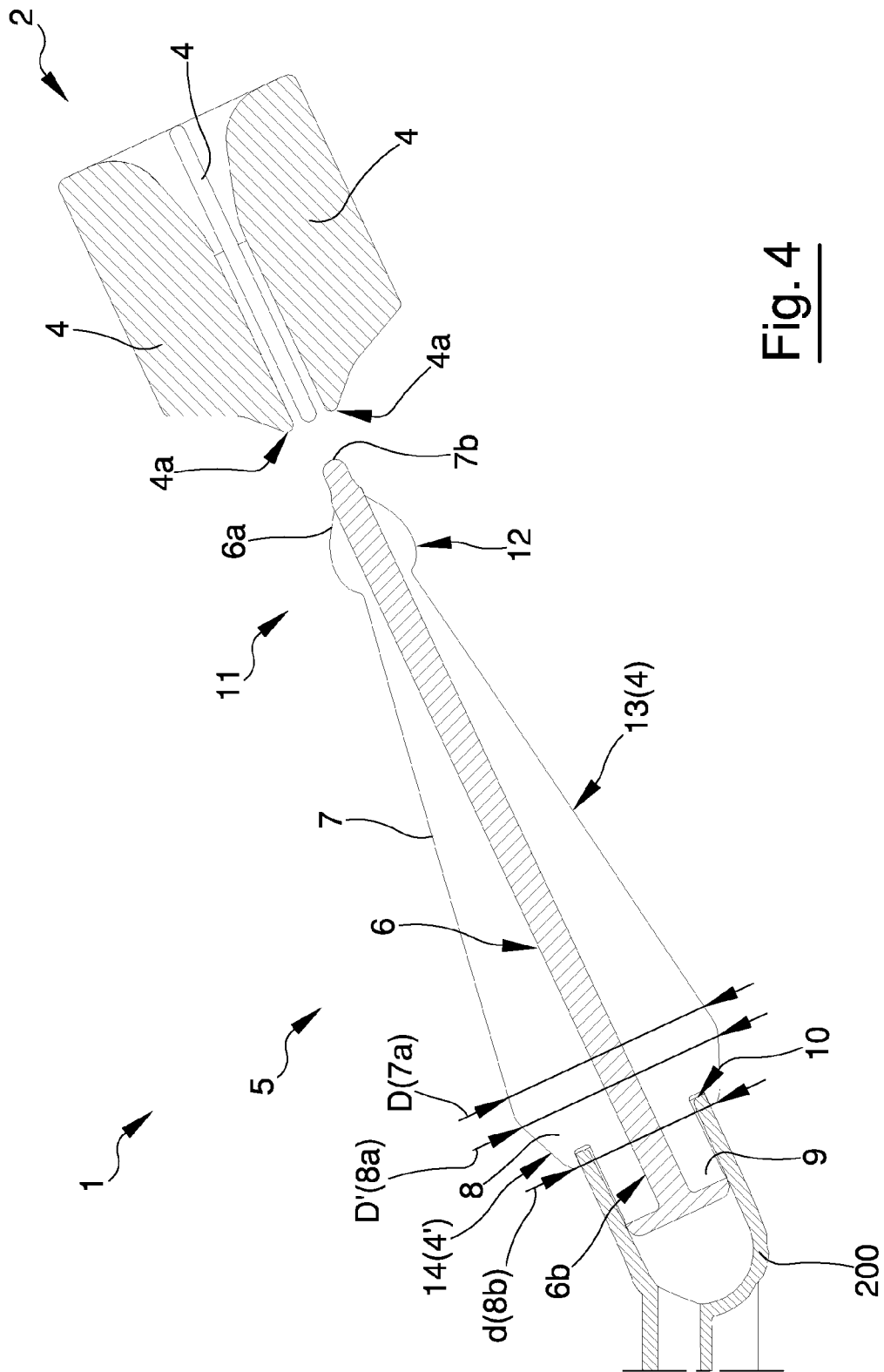
FIG. 4 is a lateral view of the device of FIG. 2 in a use configuration.

The distal end 8b of the first portion 8 is couplable to a tube 200 of a releasing pistol for legating tissues (not illustrated), as can be seen in FIG. 4.

The coupling mode will be more fully explained herein below.

With particular reference to FIG. 4, the proximal end 8a is contiguous to the base 7a and the external diameter D of the base 7a exhibits a same dimension as the external diameter D' of the proximal end 8a.

More precisely, the external diameter D of the base 7a coincides with the external diameter D' of the proximal end 8a.

In this way the loading of the rubber ring 100 on the body 5 is much easier.

In fact, the rubber 100, having crossed the substantially conical first portion 7, by means of the pushing of the pushing means 2 and by effect of its own elastic force, autonomously translates along the second portion 8 up to reaching the housing seating of the tubular body 200.

Consequently the pushing means 2 are only operative for a tract of the run thereof along the loading body, i.e. they are operative up until the rubber ring 100 has crossed the external diameter D' of the second tract 8.

The conformation of the plurality of grooves 6 enables however the sliding of the pushing means 2 along the whole loading body 5.

This is in order to enable the operator to perform the loading, in a traditional way, without seeing the device 1 and thus enabling the operator to focus her or his attention on the patient.

With reference to the plurality of grooves 6, each groove 6 exhibits an extension over the whole loading body 5.

More precisely, each groove belonging to the plurality of grooves 6 exhibits a first end 6a located in proximity of the apex 7b of the substantially conical first portion 7, and a second end 6b terminating in proximity of the cylindrical portion 9.

At least one of the grooves exhibits an abutting element 6c terminating before the second end 6b of the remaining grooves.

In this way it is possible to block the course of the pushing means 2 with respect to the loading body 5 by providing an endrun stop for the pushing means 2.

Similarly the two components can be pre-assembled with a constraint between the two components such that when the device 1 is received the loading body 5 or the pushing means 2 is constrained to the relative component.

The second portion 8 exhibits a seating 10 at the distal end 8b.

The seating 10, which is substantially annular, functions as a housing seating of the tube 200 of a pistol (not illustrated) for elastic ligature of tissues.

As can be seen in FIG. 4, the second distal end 8b of the second portion 8 is co-penetrable by the tube 200.

In this way the distal end 8a and the tube 201 of the pistol does not generate any intermediate space, such that the rubber ring 100 is facilitated to position on periphery of the tube 200.

If there is an accidental detachment of the loading body 5 from the tube 200, the rubber ring 100, by action of the pushing means 2, tends to position on the cylindrical portion 9.

Thanks to the prolonged extension of the plurality of guides 6, the operator, following the run of the pushing means 2, pushes the rubber ring 100 along the cylindrical body 9 and thus obtains an easy recuperation of the rubber ring 100.

The substantially conical first portion 7 thus exhibits the pre-loading means 11.

The pre-loading means 11, located between the base 7 and the apex 7b, are defined by a broadening of section of the substantially conical first portion 7.

The pre-loading means 11 are more preferably located in proximity of the apex 7b.

As can be seen in the figures, the pre-loading means are preferably defined by an ogive body 12.

In this way the operator can insert the rubber ring 100 onto the loading body 5, locating it downstream of the pre-loading means 11, and thereafter apply thereto the pushing means 2 in order to complete the loading of the rubber ring onto the pistol.

In the same way, the pre-loading means enable the device 1 to be made for a single-use application.

The device could be distributed directly by the producer with the rubber ring 100 already installed on the loading body 5 and located downstream of the pre-loading means 11.

In this way the operator is able to load the rubber ring 100 by sliding the pushing means 2 along the loading body 5 and thus without touching the rubber ring.

Figure 3:
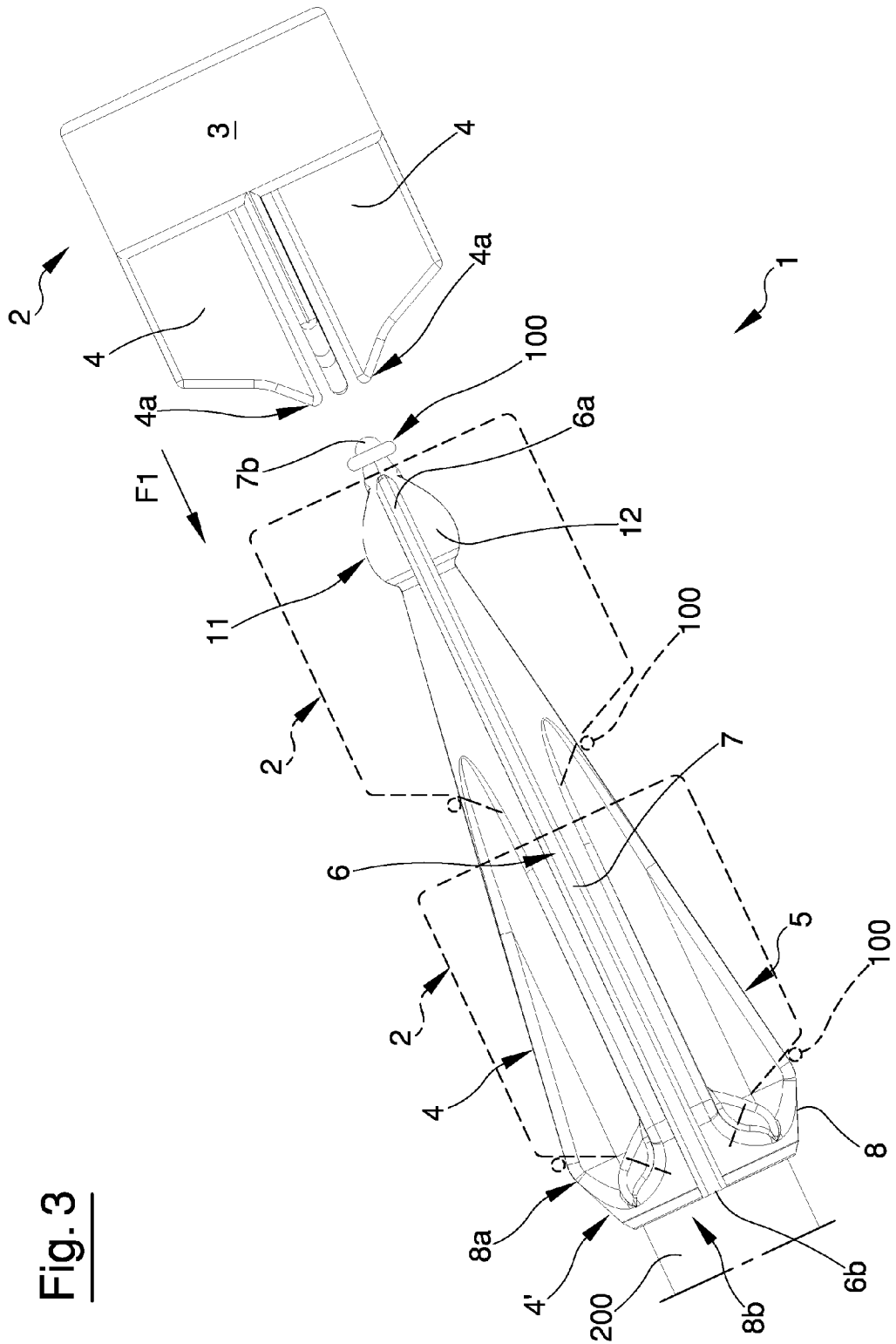
FIG. 3 is a lateral view of the device of FIG. 2 illustrating a simulation of loading a rubber ring.

As can be seen in FIGS. 1 and 3, the device 1 for stretching a rubber ring 100 exhibits a further embodiment.

The substantially conical first portion 7 is defined by a first plurality of risers 13.

Each riser 13 is uniformly subdivided and surrounds a corresponding groove 6.

Seen from the rear, i.e. with the apex 7b, as it were, entering the sheet, the plurality of risers 13 surrounds a cross, the cross being defined in negative by the plurality of grooves 6.

In other words the plurality of risers 13 defines pairs of L shapes, each arranged specularly to a contiguous pair with respect to an imaginary horizontal or vertical plane.

The first plurality of risers 13 defines first generatrices G of the conical portion.

In the same way, the second portion 8 too is defined by a second plurality of risers 14.

The second plurality of risers 14 preferably follows the first plurality 13 and exhibits a same arrangement thereas.

The second plurality of risers 14 also defines second generatrices G' of the preferably truncoconical second portion 8.

The first plurality of risers 13 and the second plurality of risers 14 internally define recesses 15 for lightening the loading body.

The recesses 15 not only lighten the loading body 5 but also reduce the contact surface of the rubber ring 100, during the sliding thereof, along the loading body 5.

The functioning of the device, schematised in FIG. 4, is the following. The operator collects a rubber ring 100 by inserting the apex 7b of the first conical portion 7 internally of the rubber ring.

The operator then pushes the rubber ring along the first conical portion 7 until the ring moves past the pre-loading means 11.

In a further embodiment, the loading body 5 can already exhibit a rubber ring 100 located downstream of the pre-loading means 11.

Thereafter the operator proceeds to couple the loading body 5 on the legating pistol (not illustrated).

During this stage it is sufficient to proceed to coupling the cylindrical portion internally of the tube 201 of the pistol.

When the tube 200 strikes against the seating 10, present on the second portion 8, the pistol is ready to be loaded with the rubber ring.

During the subsequent stage the operator takes the pushing means 2 and slides them along the loading body 5 (in the direction indicated in FIG. 1 by F1), and pushes the ring up to when it has crossed the substantially conical first portion 7.

As soon as the ring 100 passes the external diameter D' of the second portion 8, thanks to the elastic properties thereof it will autonomously slide on the whole second portion 8, stopping on the tube 201 without any further manoeuvring on the part of the operator.

The invention attains the set aims, and obviates the drawbacks noted in the prior art.

Primarily, the conformation of the loading body 5 enables an easy loading of the rubber ring 100 on the tube 200 of the legating pistol.

The arrangement of a section having a decreasing section downstream of the substantially conical first portion 7 enables the ring 100, after having gone past the conical portion 7, to translate autonomously up to being positioned on the tube 200.

The seating 10 located on the distal end 8b drastically reduces the occurrence of loading errors of the rubber ring 100 on the tube 200.

The portion of the tube 200, couplable internally of the seating 10, enables a continuity of surface to be obtained between the loading body 5 and the tube 200, preventing the rubber ring 100 from becoming positioned on the cylindrical terminal portion 9.

Even should the rubber ring 100 erroneously become located on the cylindrical portion 9, the elongate conformation of the grooves 6, i.e. crossing the whole loading body 5, enables easy recuperation of the rubber ring 100 by simply prolonging the action of the pushing means 2 on the body 5.

The presence of the pre-loading means 11 facilitates the loading operations of the rubber ring 100 on the loading body 5.

Once the ring 100 has been manually inserted and pushed downstream of the pre-loading means 11, the loading body 5 can be manoeuvred without the ring 100 being newly disconnected therefrom.

In the same way the presence of the pre-loading means enables a single-use device for stretching a rubber ring 100 to be realised.

Finally, the plurality of risers 13 and 14 of the second embodiment of the loading body 5 drastically reduces the external surface thereof and consequently the contact surface with the rubber ring 100.

This facilitates a reduction in friction during the loading operation and consequently a reduction in the tensional stresses to which the rubber ring 100 is subjected during the loading operation.

The invention claimed is:

1. A device for stretching a plastic ring, comprising:
pushing means defined by a hollow body internally of which a plurality of ribs develop;
a loading body for at least a rubber band, having a prevalent development along a direction and exhibiting a plurality of grooves for facilitating sliding along the direction of the plurality of ribs on the corresponding plurality of grooves; the loading body comprising:
a first substantially conical portion exhibiting a base, having an external diameter and an apex;
a second portion exhibiting a proximal end, having an external diameter and a distal end, having an external diameter; the proximal end exhibiting the external diameter which is greater than the external diameter of the distal end;
the proximal end being contiguous to the base and the external diameter of the base exhibiting a same length as the external diameter of the proximal end;
wherein the second portion is truncoconical, is located downstream of the base of the first substantially conical portion and exhibits, starting from the external diameter of the base of the first substantially conical portion, a transverse section having a decreasing progression.

2. The device of claim 1, wherein the first proximal end of the second portion coincides with the base of the first substantially-conical portion in order to facilitate, during the loading of the rubber band by the pushing means, first a stretching of the rubber band along the first substantially-conical portion followed by an elastic returning of the rubber band along the second portion.

3. The device of claim 1, wherein it further comprises a cylindrical portion located downstream of the second portion.

4. The device of claim 3, wherein the plurality of grooves extends along all of the loading body.

5. The device of claim 4, wherein each groove belonging to the plurality of grooves exhibits a first end which is located in proximity of the apex and a second end which terminates in proximity of the cylindrical portion, for facilitating sliding of the pushing means throughout the whole extension of the first conical portion and the second portion.

6. The device of claim 1, wherein the distal end exhibits a seating for facilitating housing internally thereof of a tube of a pistol for elastic ligature of tissues.

7. The device of claim 1, wherein it further comprises means for pre-loading, defined by a broadening of section of the first conical portion located between the apex and the base.

8. The device of claim 1, wherein the means for pre-loading are preferably defined by an ogive cone body.

9. The device of claim 1, wherein the substantially-conical first portion is defined by a first plurality of risers defining first generatrices of the conical portion.

10. The device of claim 1, wherein the substantially-conical second portion is defined by a second plurality of risers defining second generatrices of the conical portion.

11. The device of claim 9, wherein the substantially-conical second portion is defined by a second plurality of risers defining second generatrices of the conical portion, and wherein the first plurality of risers and the second plurality of risers internally define respective recesses for lightening the loading body.

12. The device of claim 1, wherein the second portion tapers in an opposite direction with respect of the first substantially conical portion.

13. The device of claim 1, wherein the proximal end of the second portion faces the first substantially conical portion and wherein the distal end of the second portion is configured to be coupled to a tube of a releasing pistol for legating tissues.

14. The device of claim 1, wherein it further comprises means for pre-loading, defined by a broadening of section of the first conical portion located between the apex and the base and in proximity of the apex.

* * * * *

UNITED STATES PATENT AND TRADEMARK OFFICE
CERTIFICATE OF CORRECTION

| | |
|---|---|
| PATENT NO. | : 8,721,320 B2 |
| APPLICATION NO. | : 13/193382 |
| DATED | : May 13, 2014 |
| INVENTOR(S) | : Bastia |

It is certified that error appears in the above-identified patent and that said Letters Patent is hereby corrected as shown below:

In the Claims

Column 7, line 9, in line 2 of Claim 8, please delete: "preferably".

Signed and Sealed this
Twenty-sixth Day of August, 2014

Michelle K. Lee
*Deputy Director of the United States Patent and Trademark Office*